(12) United States Patent
Naya

(10) Patent No.: US 6,417,925 B1
(45) Date of Patent: Jul. 9, 2002

(54) SURFACE PLASMON SENSOR FOR ANALYZING LIQUID SAMPLE OR HUMID ATMOSPHERE

(75) Inventor: Masayuki Naya, Kaisei-machi (JP)

(73) Assignee: Fuji Photo Film Co., Ltd., Kanagawa-Ken (JP)

( * ) Notice: Subject to any disclaimer, the term of this patent is extended or adjusted under 35 U.S.C. 154(b) by 0 days.

(21) Appl. No.: 09/645,355

(22) Filed: Aug. 25, 2000

(30) Foreign Application Priority Data

Aug. 26, 1999 (JP) .......................................... 11-239120

(51) Int. Cl.$^7$ .......................... G01N 21/41; G01N 21/55
(52) U.S. Cl. ........................................ 356/445; 356/128
(58) Field of Search ................................ 356/445, 318, 356/127–129, 132, 135, 136, 311, 317; 250/573, 574, 576; 422/82.05, 82.09, 68.1; 435/808; 436/805

(56) References Cited

U.S. PATENT DOCUMENTS

| | | | |
|---|---|---|---|
| 4,997,278 A | * 3/1991 | Finlan et al. | ................ 356/128 |
| 5,055,265 A | * 10/1991 | Finlan | ..................... 422/82.05 |
| 5,064,619 A | * 11/1991 | Finlan | ..................... 422/82.05 |

FOREIGN PATENT DOCUMENTS

| | | | |
|---|---|---|---|
| EP | 0 805 347 A2 | 11/1997 | .......... G01N/21/55 |
| EP | 0 834 848 A2 | 4/1998 | .......... G08C/17/00 |
| JP | 6-167443 | 6/1994 | .......... G01N/21/27 |

OTHER PUBLICATIONS

Japanese Abstract No. 10281982, dated Oct. 23, 1998.
J.D. Richards, et al.; "Surface–Plasmon Excitation Using a Polarization–Preserving Optical Fiber and an Index–Matching Fluid Optical Cell", Jun. 1, 1993; No. 16; pp. 2901–2906.

\* cited by examiner

Primary Examiner—Michael P. Stafira
(74) Attorney, Agent, or Firm—Sughrue Mion, PLLC

(57) ABSTRACT

A surface plasmon sensor which can be placed under a liquid sample or in a humid atmosphere during operation. The surface plasmon sensor is constituted of a dielectric block 11, a metal film 12 which is superposed on one surface of the dielectric block 11, a light source 14 for generating a light beam 13, a front optical system 15 which enables the light beam 13 to realize a variety of angles of incidence on an interface 11a between the dielectric block 11 and the metal film 12, each of the angles satisfying a condition for total reflection on the interface 11a, including those angles satisfying a condition for the surface plasmon resonance, and a photodetector 16 which detects a state of the surface plasmon resonance by measuring intensity of the light beam 13 after the light beam 13 is totally reflected at the interface 11a. The dielectric block 11, the light source 14, the front optical system 15 and the photodetector 16 of the surface plasmon sensor are housed in a box 20 having a waterproof structure keeping the metal film 12 on the dielectric block 11 in contact with an external atmosphere.

16 Claims, 7 Drawing Sheets

F I G . 4
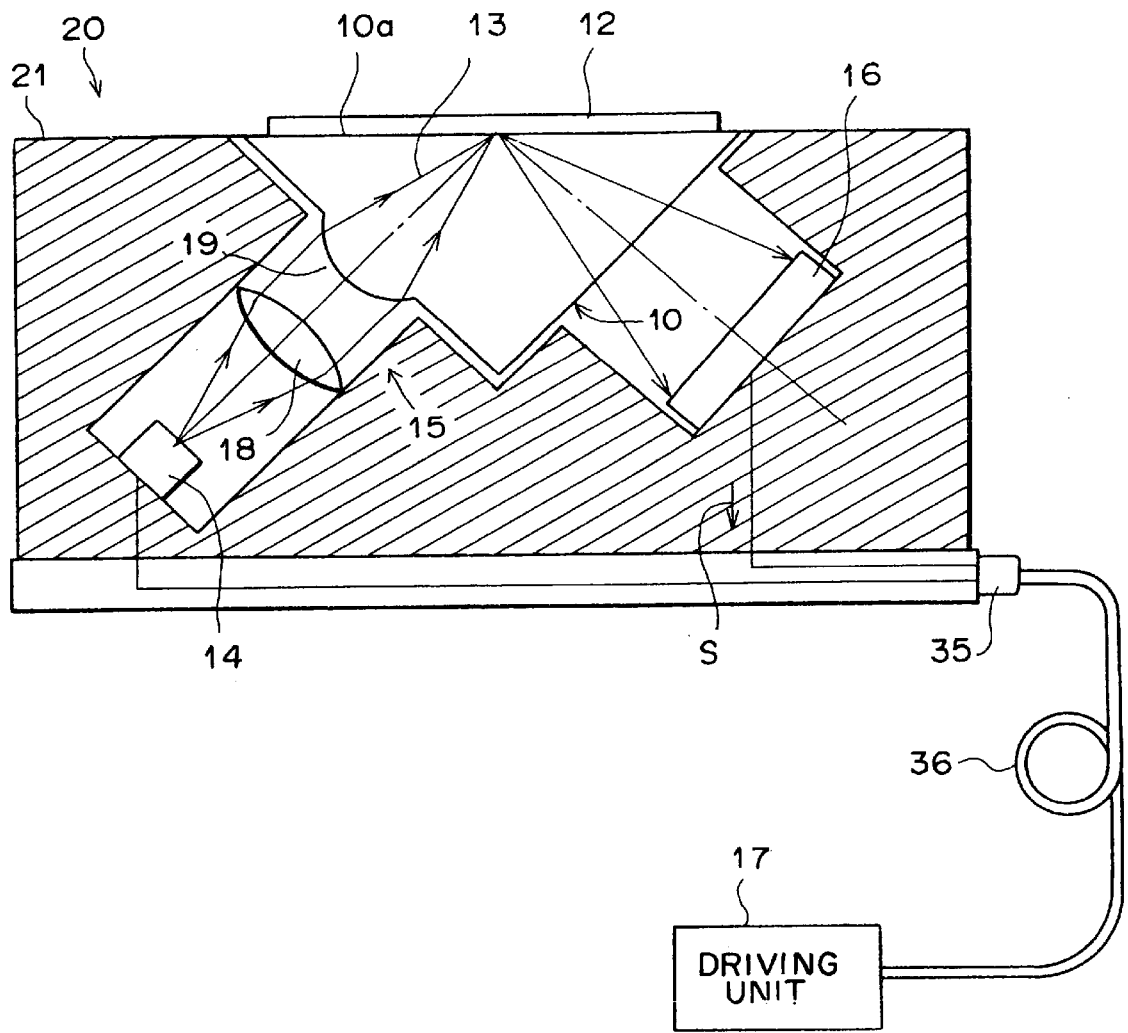

SURFACE PLASMON SENSOR FOR ANALYZING LIQUID SAMPLE OR HUMID ATMOSPHERE

BACKGROUND OF THE INVENTION

1. Field of the Invention

The present invention relates to a surface plasmon sensor used for quantitative analysis based on induction of surface plasmon, and more specifically, relates to a surface plasmon sensor which is capable of analyzing a liquid sample while being soaked under the liquid sample.

2. Description of the Related Art

Collective vibration of free electrons in metal causes compression waves called plasma waves. A quantized state of the plasma waves induced on a metal surface is called surface plasmon.

Heretofore, a variety of surface plasmon sensors have been suggested for use in quantitative analysis in which quantity of a substance contained in a sample is estimated based on an excitation phenomenon of the surface plasmon induced by optical waves. One of the most popular surface plasmon sensors is the one employing a system named the Kretschmann configuration (e.g. Japanese Unexamined Patent Publication No. 6(1994)-167443).

The surface plasmon sensor employing the Kretschmann configuration is basically constituted of a dielectric block in, for example, a prism-like shape, a metal film which is superposed on one surface of the dielectric block and is in contact with the sample, a light source for generating a light beam, an optical system which enables the light beam to realize a variety of angles of incidence on an interface between the dielectric block and the metal film, each of the angles satisfying a condition for total reflection on the interface, including those angles satisfying a condition for surface plasmon resonance, and photodetection means which detects a state of the surface plasmon resonance by measuring intensity of the light beam after the light beam is totally reflected at the interface.

A variety of angles of incidence as described above may be obtained with a light beam of a comparatively small beam diameter which is allowed to vary its angle of incidence with respect to the interface, or with a light beam of a comparatively large beam diameter which can be regarded as a group of beam components having different angles of incidence with respect to the interface and which can be made to focus on the interface. In the former case, the light beam is reflected with a variety of angles of reflection as the angle of incidence is varied, and the reflected light beam may be detected with a small, photodetector which moves in a motion synchronized with the change of the angle of incidence or may be detected with an area sensor which extends in an angular direction in which the angle of reflection varies. In the latter case, the reflected light beam may be detected with an area sensor which extends in a certain direction to receive all the beam components reflected with different angles of reflection.

In the surface: plasmon sensor having the above constitution, evanescent waves with a certain electrical field distribution are induced in the sample kept in contact with the metal film when the light beam reaches the metal film with a specific angle of incidence $\theta_{SP}$ which is equal to or larger than the angle for total reflection, and then the evanescent waves excite the surface plasmon on an interface between the metal film and the sample. When wave number matching occurs, i.e. when the size of a wave number vector of the evanescent waves is equal to a wave number of the surface plasmon, the intensity of the light beam after being totally reflected at the interface between the dielectric block and the metal film drops sharply because the evanescent waves and the surface plasmon come into a resonance state and energy carried by the light beam is consumed by the surface plasmon.

The resonance as described above occurs only when the incident beam is a beam of p-polarized light. Thus, it is required to adjust a setting of the light beam in advance so that the light beam reaches the metal film as the beam of the p-polarized light. The wave number of the surface plasmon can be calculated from the angle of incidence $\theta_{SP}$ at which the attenuated total reflection (ATR) occurs, and then a dielectric constant of the sample can be derived using the following relationship, $$K_{SP}(\omega) = \frac{\omega}{c} \sqrt{\frac{\varepsilon_m(\omega)\varepsilon_s}{\varepsilon_m(\omega) + \varepsilon_s}}$$

in which $K_{SP}$ is the wave number of the surface plasmon, $\omega$ is an angular frequency of the surface plasmon, c is the light speed in a vacuum, $\varepsilon_m$ is a dielectric constant of the metal, and $\varepsilon_s$ is the dielectric constant of the sample.

Once the dielectric constant of the sample $\varepsilon_s$ is derived, density of a specific substance within the sample can be estimated based on an appropriate calibration curve etc. In summary, the quantitative analysis of the specific substance contained in the sample can be performed by measuring the angle of incidence $\theta_{SP}$ at which the intensity of the reflected light beam drops sharply.

Beside the surface plasmon sensor of the above-described constitution, a surface plasmon sensor of another type called a long range type surface plasmon sensor is also widely known, the surface plasmon sensor realizing the quantitative analysis with higher sensitivity by providing a dielectric film layer which has a refractive index different from that of the dielectric block between the metal film and the dielectric block.

SUMMARY OF THE INVENTION

The existing surface plasmon sensors as described above have sometimes been used for measuring alcohol density of spirits during their manufacturing process, quality of water in a river, etc. However, there has been a problem in such cases that the existing surface plasmon sensors require an effort-taking procedure of sampling a small amount of the sample to be analyzed, e.g. the water in the river, and dropping the sample into a sample cell (a recessed portion for holding the sample therein) to hold the sample therein so that the sample comes into contact with the metal film.

The object of the present invention is to solve the problem by providing a surface plasmon sensor with which a mass of a liquid sample may be analyzed with simple procedures.

A first surface plasmon sensor according to the present invention is constituted of a dielectric block, a metal film, a light source for generating a light beam, an optical system, and photodetection means the same as the existing surface plasmon sensor described above, but the dielectric block, the light source, the optical system and the photodetection means are housed in a box having a waterproof structure keeping the metal film on the dielectric block in contact with an external atmosphere.

A second surface plasmon sensor according to the present invention is constituted of a dielectric block, a metal film, a dielectric film layer provided between the metal film and the dielectric block, a light source for generating a light beam, an optical system, and photodetection means the same as the existing long range type surface plasmon sensor described above, but the dielectric block, the dielectric film layer, the light source, the optical system and the photodetection means are housed in a box of having waterproof structure keeping the metal film on the dielectric block in contact with an external atmosphere.

An appropriate metal film to be used in the surface plasmon sensor according to the present invention may be selected from a group :of metal films including a gold film, a silver film, a copper film and an aluminum film.

In the surface plasmon sensor of the present invention, it is desirable to form a replaceable sensor chip constituted of at least a part of the dielectric block and the metal film superposed thereon.

Further, in the surface plasmon sensor of the present invention, a bonding substance which bonds to a specific substance may be applied fixedly on a surface of the metal film. A pair of an antigen and an antibody, the pair which is capable of antigen-antibody reaction, is one example of a combination of the specific substance and the bonding substance.

With the first surface plasmon sensor according to the present invention, the liquid sample may be easily brought into contact with the metal film by simply soaking the box having the waterproof structure under the liquid sample, because the dielectric block, the light source, the optical system and the photodetection means are housed in the box keeping the metal film on the dielectric block in contact with the external atmosphere. In this state, the surface plasmon sensor is able to perform the analysis of the sample in the same way as the existing surface plasmon sensor does.

As the box in which the dielectric block, the light source, the optical system and the photodetection means are housed has a waterproof structure, the liquid sample does not penetrate into the inner area of the box to have any detrimental effect on the dielectric block, the light source, the optical system or the photodetection means, even if the box is soaked under the liquid sample or the box is exposed to a humid atmosphere for the analysis thereof.

The second surface plasmon sensor according to the present invention is different from the first surface plasmon sensor essentially only in that the second surface plasmon sensor is provided with the dielectric film layer in addition to the dielectric block, the light source, the optical system and the photodetection means. As the dielectric film layer is also housed in the box having the waterproof structure, the second surface plasmon sensor shows the same advantage as the first surface plasmon sensor.

BRIEF DESCRIPTION OF THE DRAWINGS

FIG. 4 is a side view of the surface plasmon sensor in accordance with the second embodiment of the present invention.

DESCRIPTION OF THE PREFERRED EMBODIMENTS

Figure 1:
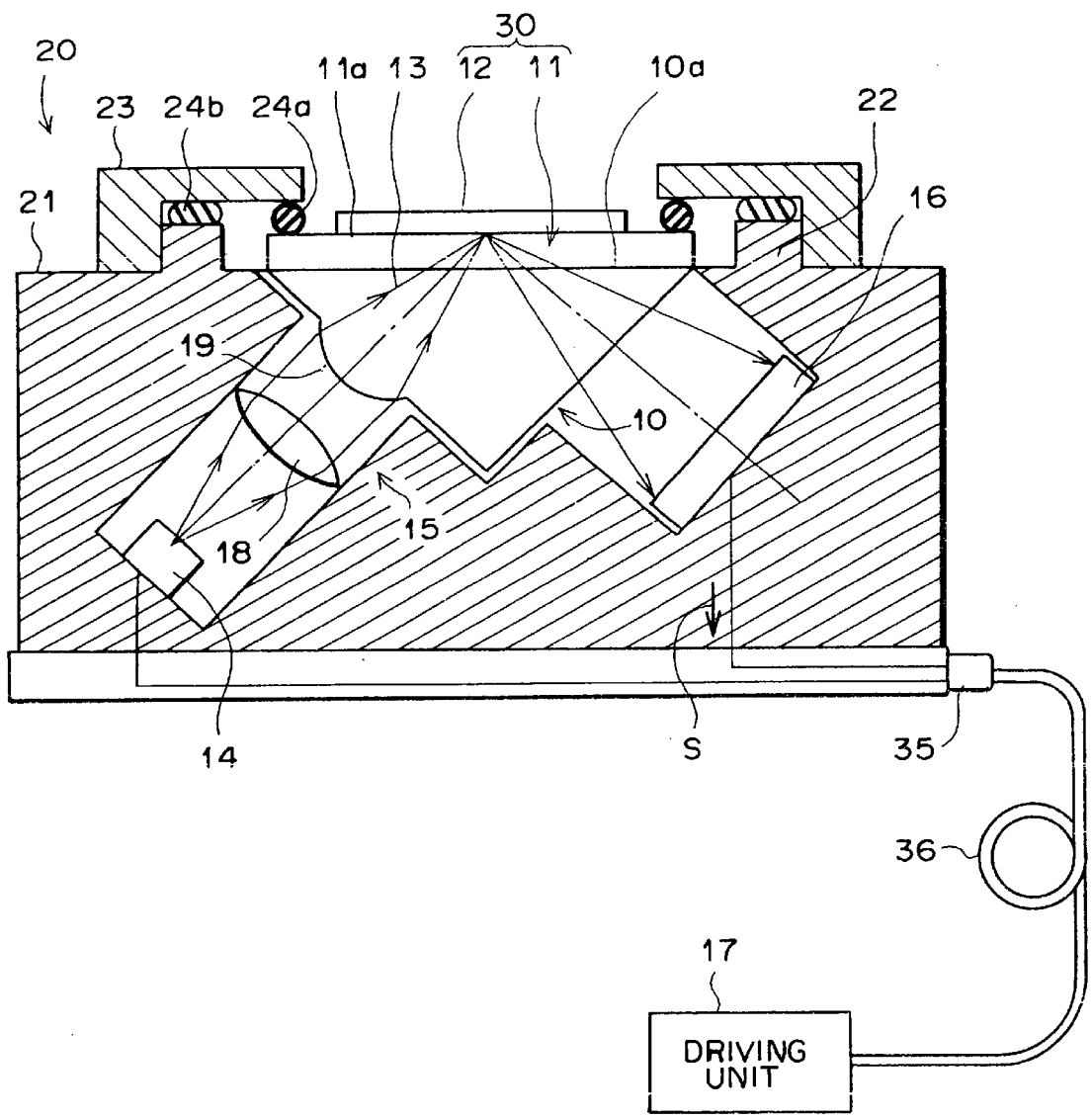
FIG. 1 is a side view of the surface plasmon sensor in accordance with the first embodiment of the present invention.
Figure 2:
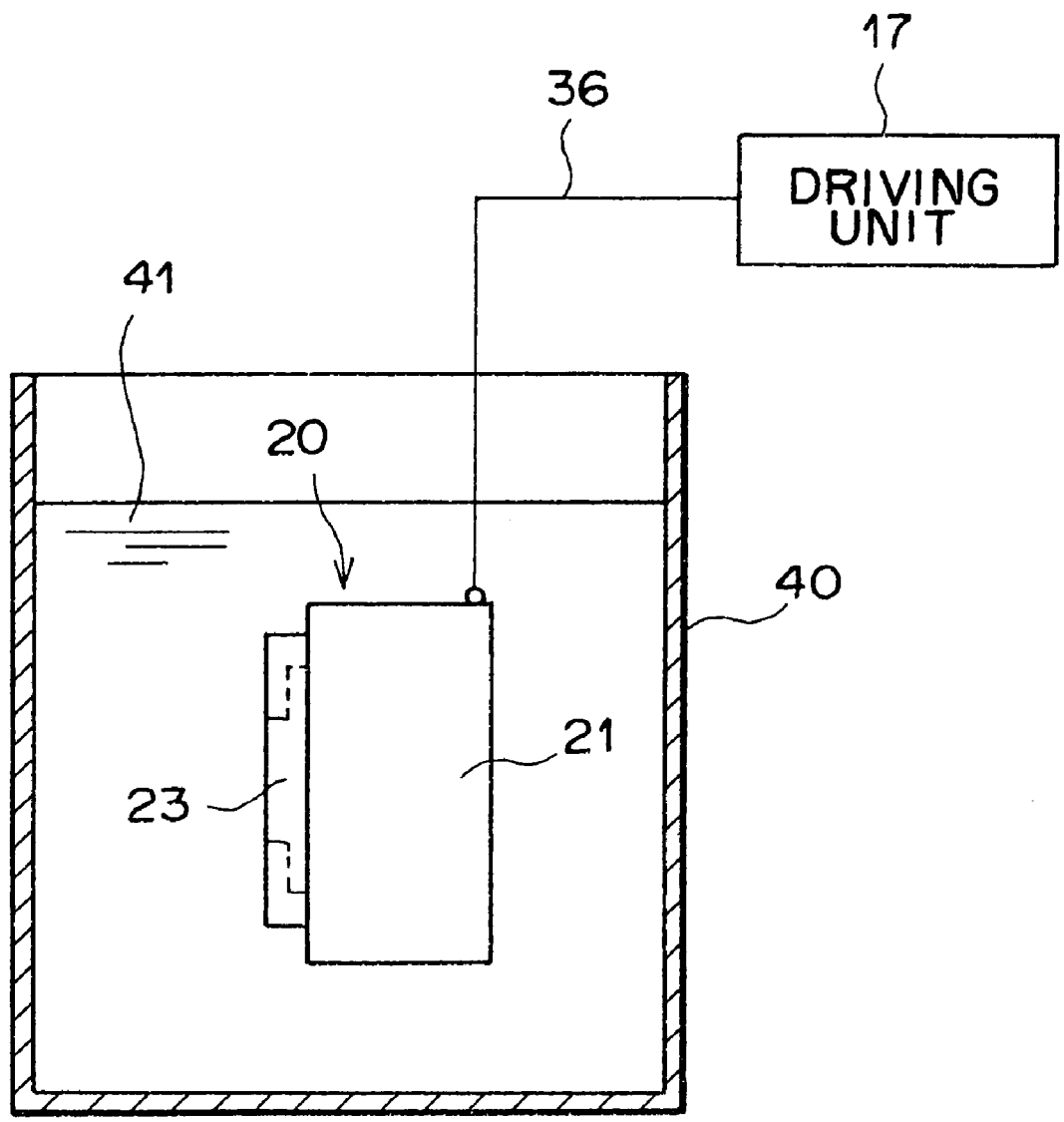
FIG. 2 is a schematic view showing usage of the surface plasmon sensor of FIG. 1.
Figure 3:
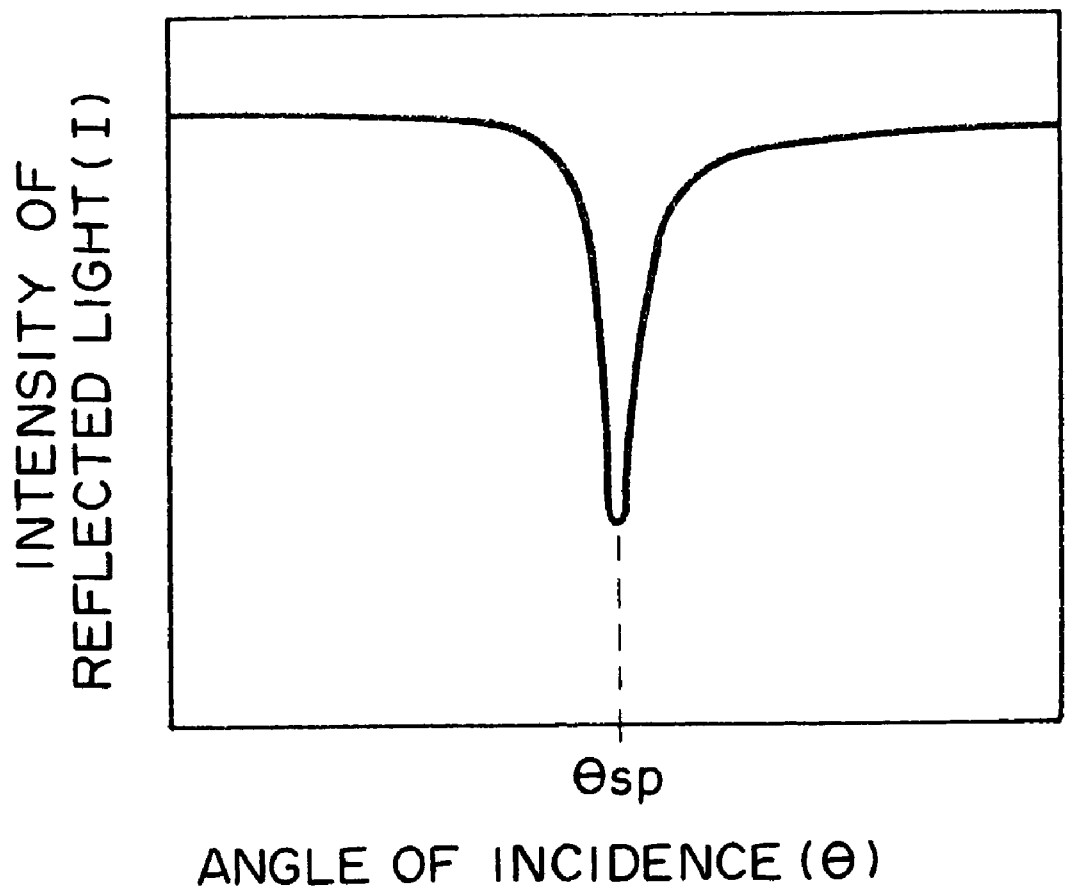
FIG. 3 is a graph showing a general relationship between an angle of incidence of a light beam and intensity of light detected by a photodetector in a surface plasmon sensor.

The first embodiment of the present invention will now be described with reference to FIGS. 1 to 3 of the accompanying drawings. FIG. 1 is a sectional side view of the surface plasmon sensor in accordance with the first embodiment of the present invention. The surface plasmon sensor shown in FIG. 1 is constituted of a prism 10 made of a glass material which is dielectric, a plate-like dielectric block 11 fixed on a surface 10a of the prism 10, a metal film 12 which is superposed on one surface of the dielectric block 11 and is made of metal, e.g. gold, silver, copper, aluminum, etc., a light source 14, e.g. a semiconductor laser, for generating a light beam (a laser beam) 13, a front optical system 15 which enables the light beam 13 to reach an interface 11a between the dielectric block 11 and the metal film 12 as a beam of p-polarized light via the prism 10 and the dielectric block 11 realizing a variety of angles of incidence on the interface 11a, a photodetector 16 for detecting a reflected beam of the light beam 13 which is totally reflected at the interface 11a, and a driving unit 17 connected with the photodetector 16 and the light source 14.

The light beam 13 is made to reach the interface 11a as the beam of the p-polarized light by fixing the light source 14 appropriately in advance so that a desired polarization direction is attained. Alternatively, the polarization direction of the light beam 13 may be controlled by means of a wave plate or a polarizing plate.

The front optical system 15 is constituted of a collimator lens 18 for collimating the light beam 13 which is emitted from the light source 14 as a diverging beam, and a collective lens 19 which is incorporated as an integral part of the prism 10 to focus the light beam 13 on the interface 11a.

The light source 14, the front optical system 15, the prism 10, the dielectric block 11 and the photodetector 16 are housed in a box 20 having a waterproof structure keeping the metal film 12 on the dielectric block 11 in contact with an external atmosphere. The box 20 includes a box body 21, a ring-like projected portion 22 projecting from an upper face of the box body 21, a cap 23 which catches the projected portion 22 using catching means (not shown) and has an aperture at a central part thereof, and packing rings 24a and 24b. The driving unit 17 is connected with the photodetector 16 and the light source 14 by means of a waterproof connector 35 and a waterproof cord 36.

The dielectric block 11 and the metal film 12 superposed thereon together form a replaceable sensor chip 30. The sensor chip 30 is fixed on the prism 10 by placing the dielectric block 11 on the surface 10a of the prism 10, placing the packing rings 24a and 24b on an upper peripheral part of the dielectric block 11 and on the projected portion 22, respectively, and then having the cap 23 catch the projected portion 22 so that the cap 23 pushes the dielectric block 11 against the prism 10 via the packing ring 24a. The dielectric block 11 is made of a material which has the same refractive index as the prism 10, and is placed on the surface 10a of the prism 10 with index-matching oil applied between the dielectric block 11 and the surface 10a.

The light beam 13 focused by the collective lens 19 as described above can be regarded as a group of beam components having different angles of incidence θ with respect to the interface 11a between the dielectric block 11 and the metal film 12. Each of the angles of incidence θ herein is equal to or larger than the angle for total reflection. Thus, the light beam 13 is totally reflected at the interface 11a, and the reflected beam can also be regarded as a group of beam components having different angles of reflection.

The photodetector 16 is constituted of a line sensor which has multiple detecting elements aligned thereon, wherein the multiple detecting elements are aligned along an angular direction in which the angles of reflection vary.

Now, processes for analyzing a sample using the surface plasmon sensor of the above constitution are described in detail. As shown in FIG. 2, the box 20 having a waterproof structure is soaked under a liquid sample 41 stored in a container 40 when analyzing the liquid sample 41, so that the metal film 12 is brought into contact with the liquid sample 41. After the box 20 is soaked, the light beam 13 is emitted toward the interface 11a between the dielectric block 11 and the metal film 12 and reaches the interface 11a via the prism 10 being focused by the collective lens 19. The light beam 13 is totally reflected at the interface 11a and then detected by the photodetector 16.

In the case of the total reflection of the light beam 13 as described above, evanescent waves penetrate into the metal film 12 through the interface 11a. When the light beam 13 reaches the interface 11a with a specific angle of incidence $\theta_{SP}$, the light beam 13 resonates with the surface plasmon which is induced on the surface of the metal film 12 by the evanescent waves, and intensity I of the reflected beam of the light beam 13 drops sharply. FIG. 3 illustrates a general relationship between the angle of incidence θ and the intensity I of the reflected beam around the specific angle of incidence $\theta_{SP}$ where the attenuated total reflection phenomenon as described above occurs.

Consequently, once the specific angle of incidence (angle of attenuated :total reflection) $\theta_{SP}$ is determined by looking over detected intensities per detecting element, wherein each of the intensities can be derived from photodetection signals S output by the photodetector 16, quantity of a specific substance contained in the liquid sample 41 can be estimated based on a predetermined curve showing a relationship between the angle of incidence θ and the intensity I of the reflected beam.

As the packing ring 24a prevents the liquid sample 41 from flowing into the inside of the box body 21 from the outside, the light source 14, the front optical system 15, the prism 10 and the photodetector 16 housed in the box body 21 never get wet in the liquid sample 41 which may have a detrimental effect thereon.

Further, as the dielectric block 11 and the metal film 12 superposed thereon together form the replaceable sensor chip 30 in this embodiment, it is possible to replace the sensor chip 30 easily and immediately in the case where, for example, the metal film 12 is deteriorated or it is desirable to replace the metal film 12 with a film of a different metal material in accordance with properties of the liquid sample 41.

Now, the second embodiment of the present invention will be described with reference to FIG. 4 of the accompanying drawings. FIG. 4 is a sectional side view of the surface plasmon sensor in accordance with the second embodiment of the present invention, wherein an element equivalent to any of the elements appearing in FIG. 1 is labeled with the identical number and explanation for such elements is not repeated below (the, same also applies in the other embodiments described hereinafter).

In this second embodiment, the function of the dielectric block is incorporated in the prism 10 and the metal film 12 is superposed on the surface 10a of the prism 10. In this case, the light beam 13 is adjusted as it enters the prism 10 so that the light beam 13 focuses on the surface 10a of the prism 10.

Though the sensor chip, which is replaceable in the first embodiment, is incapable of replacement, the box 20 attains higher waterproof capability in this second embodiment.

Figure 5:
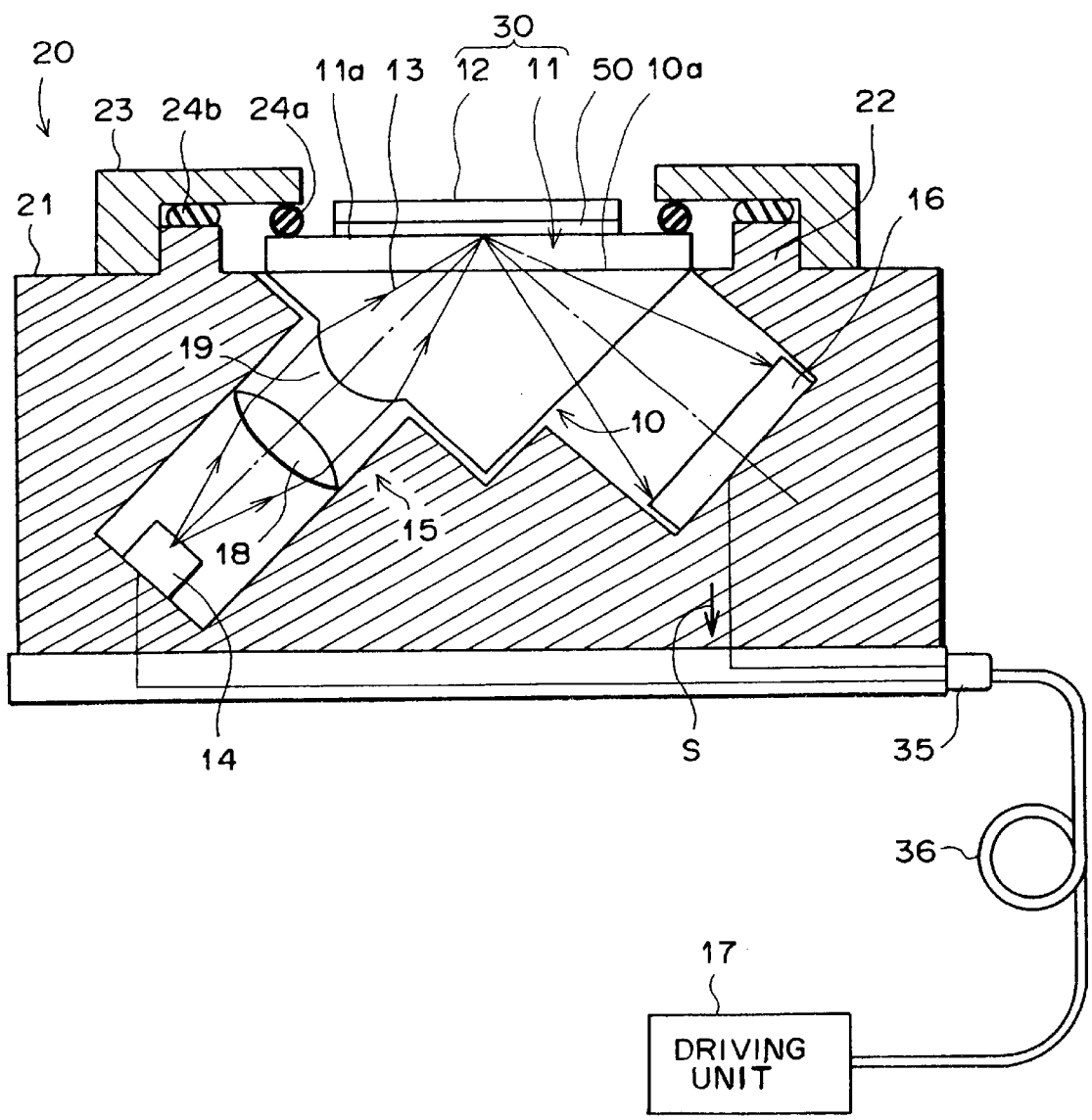
FIG. 5 is a side view of the surface plasmon sensor in accordance with the third embodiment of the present invention.

Next, the third embodiment of the present invention will be described with reference to FIG. 5 which shows a sectional side view of the surface plasmon sensor in accordance with the third embodiment. This third embodiment adopts a constitution which enables induction of the surface plasmon resonance of the long range type described in the section introducing the related art.

The constitution: of the surface plasmon sensor of this embodiment is almost same as that of the first embodiment illustrated in FIG. 1, but a difference lies in that the surface plasmon sensor of this embodiment is provided with a dielectric film layer: 50 between the dielectric block 11 and the metal film 12, wherein the dielectric film layer 50 and the dielectric block 11 have different refractive indices (the refractive index of the dielectric film layer 50 is assumed to be smaller in the description herein).

As the dielectric film layer 50 having the refractive index smaller than that of the dielectric block 11 is provided on the dielectric block 11 and the metal film 12 is superposed thereon in this embodiment, the occurrence of the surface plasmon resonance is limited in a narrow range of wave number, namely the range in which the surface plasmon resonates with a propagation mode of the dielectric film layer 50. Therefore, the photodetection signal S may change remarkably by changing the angle of incidence only slightly and higher sensitivity can be realized.

Figure 6:
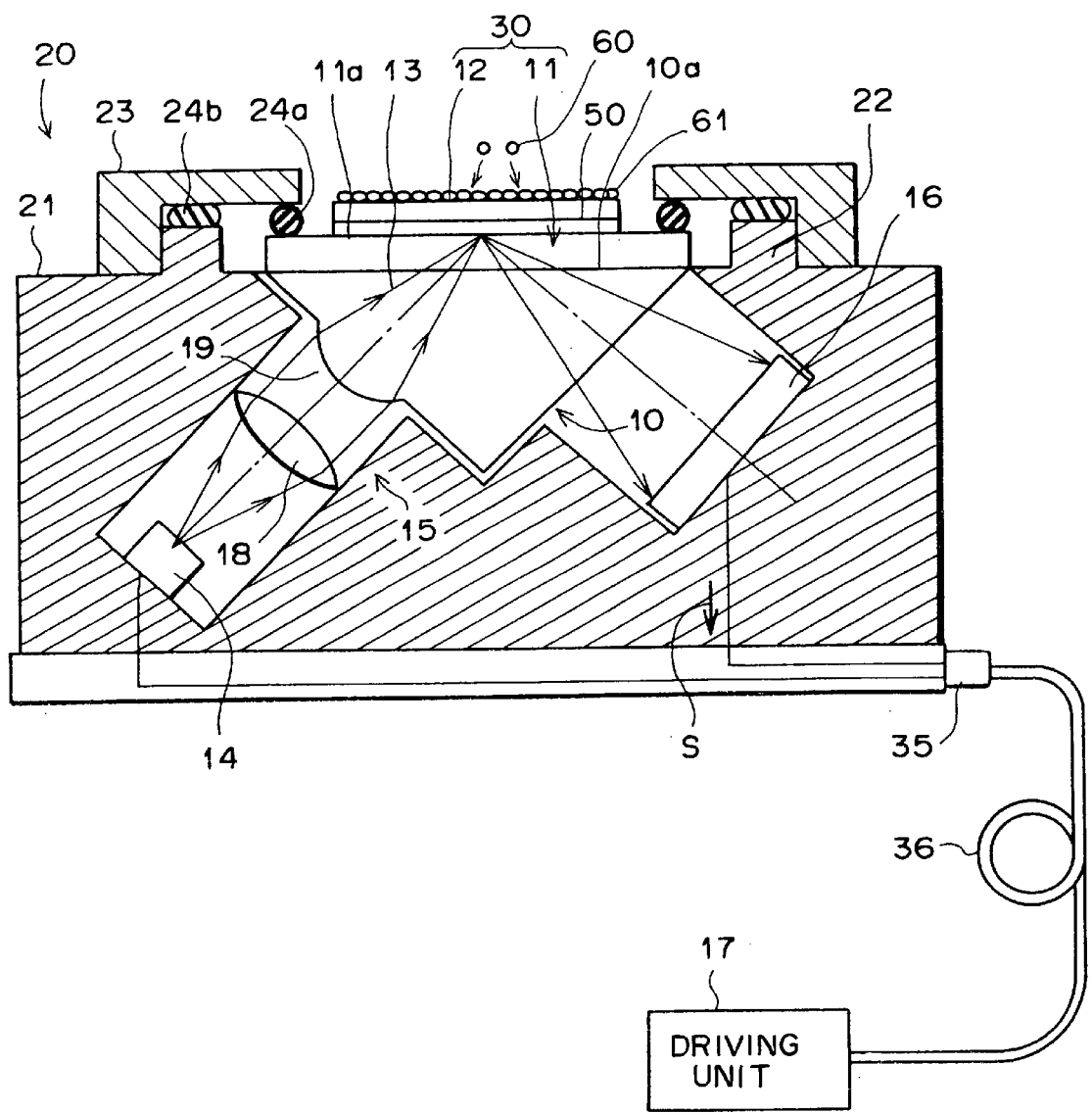
FIG. 6 is a side view of the surface plasmon sensor in accordance with the fourth embodiment of the present invention.

The fourth embodiment of the present invention will be described with reference to FIG. 6 which shows a sectional side view of the surface plasmon sensor in accordance with the fourth embodiment. The constitution of the surface plasmon sensor of this fourth embodiment is almost the same as that of the third embodiment illustrated in FIG. 5, but a difference lies in that the surface plasmon sensor of this embodiment includes a bonding substance 61 which is applied fixedly on the surface of the metal film 12 and which is capable of bonding to a specific substance 60 contained in the liquid sample.

A pair of an antigen and an antibody is one example of a combination of the specific substance 60 and the bonding substance 61. In that case, antigen-antibody reaction can be detected based on the:angle of attenuated total reflection $\theta_{SP}$.

Figure 7:
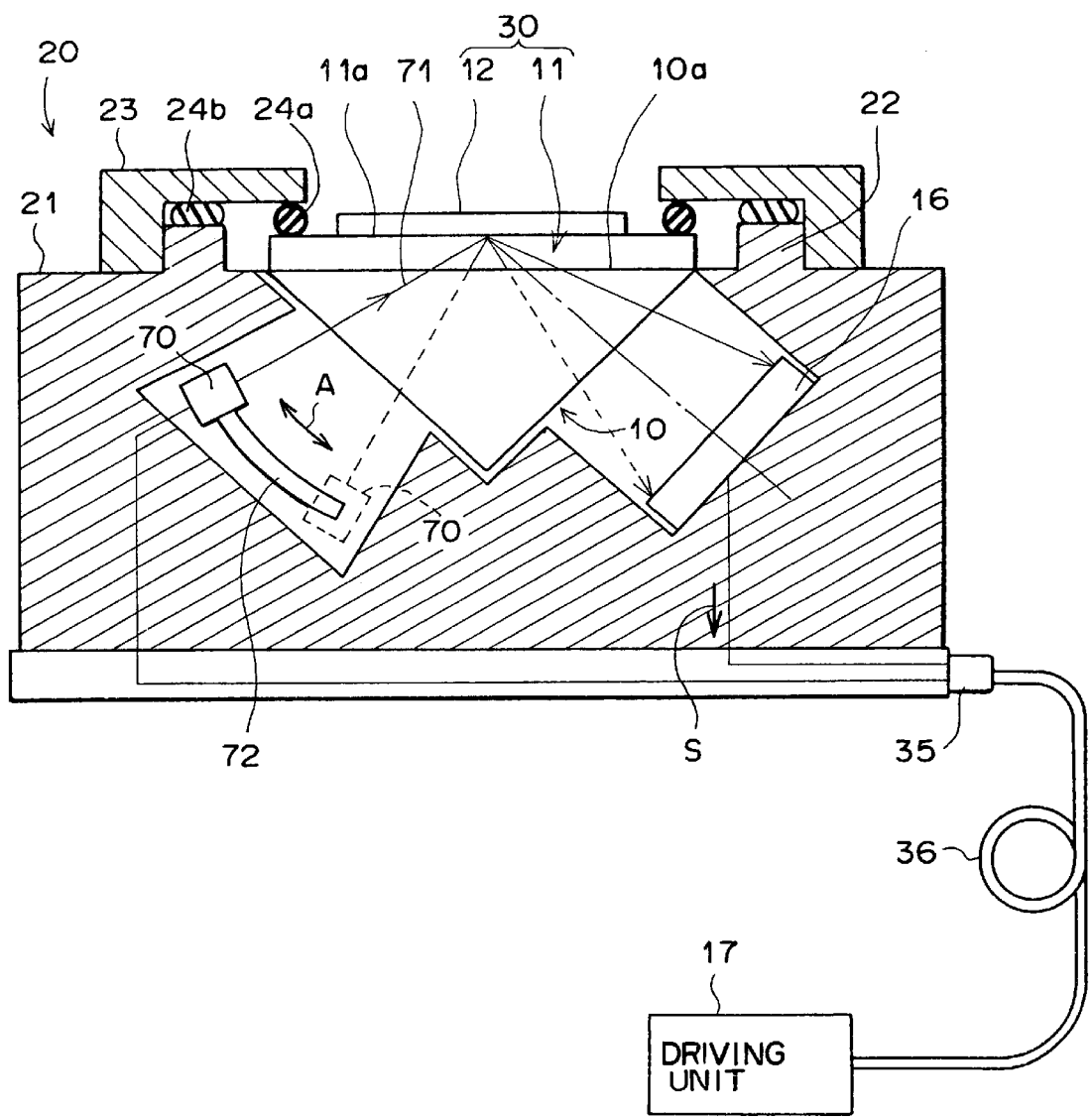
FIG. 7 is a side view of the surface plasmon sensor in accordance with the fifth embodiment of the present invention.

Finally, the fifth embodiment of the present invention will be described with reference to FIG. 7 which shows a sectional side view of the surface plasmon sensor in accordance with the fifth embodiment. The constitution of the surface plasmon sensor of this fifth embodiment is almost the same as that of the first embodiment illustrated in FIG. 1, but the surface plasmon sensor of this embodiment has a light source and a front optical system different from those in the first embodiment.

In this embodiment, the light source 70 generates a single light beam 71 with a small beam diameter, and is capable of being moved in directions of A by mechanical beam deflecting means 72. The angle of incidence θ as the light beam 71 reaches the interface 11a between the dielectric block 11 and the metal film 12 may be varied by moving the light source 70 in the directions of A.

In this embodiment, as well as in the other embodiments, the polarization direction of the light beam 71 may be controlled by means of the wave plate or the polarizing plate to make the light beam 71 reach the interface 11a as the beam of the p-polarized light.

The present invention may be applied to surface plasmon sensors of various types other than the surface plasmon sensors as described above. For example, the present invention may be applied to a surface plasmon sensor which measures two-dimensional distribution of a property of a sample kept in contact with a metal film of the surface plasmon sensor.

In addition, all of the contents of the Japanese Patent Application No. 11(1999)-239120 are incorporated into this specification by reference.

What is claimed is:

1. A surface plasmon sensor comprising
   a dielectric block,
   a metal film superposed on one surface of the dielectric block,
   a light source for generating a light beam,
   an optical system which enables the light beam to realize a variety of angles of incidence on an interface between the dielectric block and the metal film, each of the angles satisfying a condition for total reflection on the interface, including those angles satisfying a condition for surface plasmon resonance,
   a photodetection means for detecting a state of the surface plasmon resonance by measuring intensity of the light beam after the light beam is totally reflected at the interface, and
   a box having a waterproof structure in which the dielectric block, the light source, the optical system and the photodetection means are housed keeping the metal film on the dielectric block in contact with an..external atmosphere, said box being watertight to be immersible in liquid and protecting at least one of said light source, said optical system, and said photodetection means from coming into contact with the liquid.

2. A surface plasmon sensor as defined in claim 1 wherein the metal film is made of gold, silver, copper or aluminum.

3. A surface plasmon sensor as defined in claim 1 wherein at least a part of the dielectric block and the metal film superposed thereon together form a replaceable sensor chip.

4. A surface plasmon sensor as defined in claim 1 wherein a bonding substance which bonds to a specific substance is applied fixedly on a surface of the metal film.

5. A surface plasmon sensor as defined in claim 4 wherein one of the, specific substance and the bonding substance is an antigen and the other is an antibody.

6. A surface plasmon sensor comprising
   a dielectric block,
   a metal film superposed on one surface of the dielectric block,
   a dielectric film layer which is provided between the metal film and the dielectric block and which has a refractive index different from a refractive index of the dielectric block,
   a light source for generating a light beam,
   an optical system which enables the light beam to realize a variety of angles of incidence on an interface between the dielectric block and the metal film, each of the angles satisfying a condition for total reflection on the interface, including those angles satisfying a condition for surface plasmon resonance,
   a photodetection means for detecting a state of the surface plasmon resonance by measuring intensity of the light beam after the light beam is totally reflected at the interface, and
   a box having a waterproof structure in which the dielectric block, the dielectric film layer, the light source, the optical system and the photodetection means are housed keeping the metal film on the dielectric block in contact with an external atmosphere, said box being watertight to be immersible in liquid and protecting at least one of said light source, said optical system, and said photodetection means from coming into contact with the liquid.

7. A surface plasmon sensor as defined in claim 6 wherein the metal film is made of gold, silver, copper or aluminum.

8. A surface plasmon sensor as defined in claim 6 wherein at least a part of the dielectric block and the metal film superposed thereon together form a replaceable sensor chip.

9. A surface plasmon sensor as defined in claim 6 wherein a bonding substance which bonds to a specific substance is applied fixedly on a surface of the metal film.

10. A surface plasmon sensor as defined in claim 9 wherein one of the specific substance and the bonding substance is an antigen and the other is an antibody.

11. A surface plasmon sensor comprising
    a dielectric block,
    a metal film superposed on one surface of the dielectric block,
    a light source for generating a light beam,
    an optical system which enables the light beam to realize a variety of angles of incidence on an interface between the dielectric block and the metal film, each of the angles satisfying a condition for total reflection on the interface, including those angles satisfying a condition for surface plasmon resonance,
    a photodetection means for detecting a state of the surface plasmon resonance by measuring intensity of the light beam after the light beam is totally reflected at the interface, and
    a box having a waterproof structure in which the dielectric block, the light source, the optical system and the photodetection means are housed keeping the metal film on the dielectric block in contact with an external atmosphere, wherein said box having a waterproof structure is watertight to be immersible in liquid and said box protects said light source and the photodetection means from coming into contact with the liquid.

12. The surface plasmon sensor of claim 11, wherein said box comprises:
    a protruding section; and
    a cap portion disposed adjacent to the protruding section, said cap portion having a height slightly greater than the protruding section and a lip segment that overlaps said protruding section, and wherein said lip segment overhangs said dielectric block.

13. The surface plasmon sensor according to claim 12, wherein said lip segment contacts first seal members against said protruding section and second seal members against said dielectric block to provide a watertight seal.

14. A surface plasmon sensor comprising
    a dielectric block,
    a metal film superposed on one surface of the dielectric block,
    a dielectric film layer which is provided between the metal film and the dielectric block and which has a refractive index different from a refractive index of the dielectric block, a light source for generating a light beam, an optical system which enables the light beam to realize a variety of angles of incidence on an interface between the dielectric block and the metal film, each of the angles satisfying a condition for total reflection on the interface, including those angles satisfying a condition for surface plasmon resonance, a photodetection means for detecting a state of the surface plasmon resonance by measuring intensity of the light beam after the light beam is totally reflected at the interface, and a box having a waterproof structure in which the dielectric block, the dielectric film layer, the light source, the optical system and the photodetection means are housed keeping the metal film on the dielectric block in contact with an external atmosphere, wherein said box having a waterproof structure is watertight to be immersible in liquid and said box protects said light source and the photodetection means from coming into contact with the liquid.

15. The surface plasmon sensor of claim 14, wherein said box comprises:

a protruding section; and a cap portion disposed adjacent to the protruding section, said cap portion having a height slightly greater than the protruding section and a lip segment that overlaps said protruding section, and wherein said lip segment overhangs said dielectric block.

16. The surface plasmon sensor according to claim 15, wherein said lip segment contacts first seal members against said protruding section and second seal members against said dielectric block to provide a watertight seal.

* * * * *